United States Patent [19]
Ruby et al.

[11] Patent Number: 5,272,068
[45] Date of Patent: Dec. 21, 1993

[54] PROCESS FOR PRODUCING IMMUNOSUPPRESSANT AGENT L-683942 BY FERMENTATION

[75] Inventors: Carolyn L. Ruby, Montclair; Susan J. Danis, Oakland; Byron H. Arison, Watchung, all of N.J.

[73] Assignee: Merck & Co., Inc., Rahway, N.J.

[21] Appl. No.: 734,039

[22] Filed: Jul. 23, 1991

Related U.S. Application Data

[63] Continuation of Ser. No. 323,653, Mar. 15, 1989, abandoned.

[51] Int. Cl.⁵ .................. C12P 17/18; C12P 17/00; C12N 1/20
[52] U.S. Cl. .................. 435/118; 435/117; 435/253.5; 435/898
[58] Field of Search .............. 435/119, 117, 253.8, 435/898

[56] References Cited

U.S. PATENT DOCUMENTS 3,094,460  6/1963  DeBoer ........................... 435/886
3,244,592  4/1966  Arai ............................... 435/119

FOREIGN PATENT DOCUMENTS 1151091  8/1983  Canada ........................... 435/898
0184162  6/1986  European Pat. Off. ............ 435/119

OTHER PUBLICATIONS

J. Antibiotics, A15, pp. 231–232, by Arai, et al.

Primary Examiner—Irene Marx
Attorney, Agent, or Firm—Robert J. North; Hesna J. Pfeiffer; J. Eric Thies

[57] ABSTRACT

Described is a new process for producing the immunosuppressant, L-683,742, a C-31 demethylated, derivative of L-683,590 (FK-520), produced under fermentation conditions utilizing the new mutant microorganism, *Streptomyces hygroscopicus* subsp. *ascomyceticus* (Merck Culture Collection MA 6646) ATCC No. 53855, being a blocked mutant of *Streptomyces hygroscopicus* subsp. *ascomyceticus* (MA 6475) ATCC No. 14891. The macrolide immunosuppressant is useful in preventing human host rejection of foreign organ transplants, e.g. bone marrow and heart transplants.

1 Claim, 5 Drawing Sheets

PROCESS FOR PRODUCING IMMUNOSUPPRESSANT AGENT L-683942 BY FERMENTATION

This is a continuation of application Ser. No. 07/323,653, filed on Mar. 15, 1989 now abandoned.

BACKGROUND OF THE INVENTION

1. Field of the Invention

This invention relates to a new process for producing the immunosuppressant agent, L-683,742, utilizing the new mutant microorganism *Streptomyces hygroscopicus* subsp. *ascomyceticus* (MA 6646) ATCC No. 53855, being a blocked mutant of *Streptomyces hygroscopicus* subsp. *ascomyceticus* (MA 6475), ATCC No. 14891. The process involves culturing the new microorganism under aerobic fermentation conditions in an aqueous carbohydrate medium containing a nitrogen nutrient.

2. Brief Description of Disclosures in the Art

In 1983, the US FDA approved cyclosporin, an extremely effective anti-rejection drug that revolutionized the field of organ transplant surgery. The drug acts by inhibiting the body's immune system from mobilizing its vast arsenal of natural protecting agents to reject the transplant's foreign protein.

As effective as the drug is in fighting transplantation rejection, it suffers drawbacks in causing kidney failure, liver damage and ulcers which in many cases can be very severe.

EPO Publication No. 0184162 to Fujisawa, hereby incorporated by reference, describes a new macrolide, immunosuppressant FK-506 which is reputed to be 100 times more potent than cyclosporin. The macrolide, as well as the structurally related FK-525, are produced by fermentation of a particular strain of *Streptomyces tsukubaensis*. Also described are the closely related macrolide immunosuppressants, FK-520 and FK-523, produced by *S. hygroscopicus* subsp. *yakushimaensis*.

U.S. Pat. No. 3,244,592 to T. Arai describes the culturing of *Streptomyces hygroscopicus var. ascomyceticus* to produce the antifungal "ascomycin".

U.S. Ser. No. 213,025 U.S. Ser. No. 213,025 (case Docket 17767) by S. T. Chen, E. S. Inamine, B. H. Arison, L. S. Wicker, (assigned to Merck & Co. Inc.) hereby incorporated by reference, discloses a new immunosuppressant agent, "demethimmunomycin", L-683,742, a C-31 demethylated analog of L-683,590 (FK-520) produced by culturing the microorganism *Actinoplanacete sp.* (MA 6559), ATCC No. 53771, in the presence of L-683,590 to effect a biotransformation of L-683,590.

There is, however, no description in the literature of the production of the immunosuppressive agent L-683,742 directly from the fermentation of a microorganism which does not require the presence of L-683,590 starting material.

New processes in this regard are constantly being searched for in the field.

SUMMARY OF THE INVENTION

It has been found that the immunosuppressant, L-683,742, can be directly obtained by the fermentation of the mutant microorganism *Streptomyces hygroscopicus* subsp. *ascomyceticus* (MA 6646) ATCC No. 53855, derived from ATCC No. 14891 (MA 6475), by the mutagenic treatment of N-methyl-N'-nitro-N-nitrosoguanidine. The fermentation does not require the presence of the macrolide immunosuppressant L-683,590, and is conducted under submerged aerobic conditions in an aqueous carbohydrate medium, containing a nitrogen nutrient, said conditions being conducted at a pH below 8.0, e.g., of about 7, for a sufficient time to produce L-683,742, (demethimmunomycin), the mono-C-31 demethylated version of L-683,590 (immunomycin), as described in Ser. No. 213,025 (Case 17767), filed Jun. 29, 1988, having the same assignee, and hereby incorporated by reference for this particular purpose. Other C-31 demethylated derivatives of L-683,590 type macrolides are also reasonably believed to be in the broth produced by the described invention process herein.

The resultant L-683,742 exhibits immunosuppressive activity, i.e., positive inhibition of T-cell activation, as demonstrated by the calcium ionophore (ionomycin) plus phorbol myristate acetate (PMA) induced T-cell stimulation assay, also referred to herein as the "T-cell proliferation assay". The principle of this assay is to measure the proliferation of mouse T lymphocytes stimulated with the combination of ionomycin plus PMA. A positive sample in this assay will inhibit T-cell proliferation, as indicated by reduced tritiated thymidine uptake.

In accordance with this invention there is provided a new process for producing an immunosuppressant, identified as a C-31 demethylated derivative of a L-683,590 type macrolide comprising the step of culturing a mutant of a *Streptomyces* which produces said C-31 demethylated derivative under submerged aerobic fermentation conditions in an aqueous carbohydrate medium containing a nitrogen nutrient at a pH below 8.0 for a sufficient time to produce the C-31 demethylated immunosuppressant.

Further provided is a new process for producing the immunosuppressant, identified as L-683,742, produced by culturing a strain of *Streptomyces hygroscopicus* subsp. *ascomyceticus* (MA 6646) ATCC No. 53855, under submerged aerobic fermentation conditions in an aqueous carbohydrate medium, containing a nitrogen nutrient, for a sufficient time to produce product L-683,742.

Also provided is the broth produced by the above process.

In addition, there is provided a new mutant microorganism, *Streptomyces hygroscopicus* subsp. *ascomyceticus* ATCC No. 53855.

DETAILED DESCRIPTION OF THE INVENTION AND PREFERRED EMBODIMENTS

Figure 1:
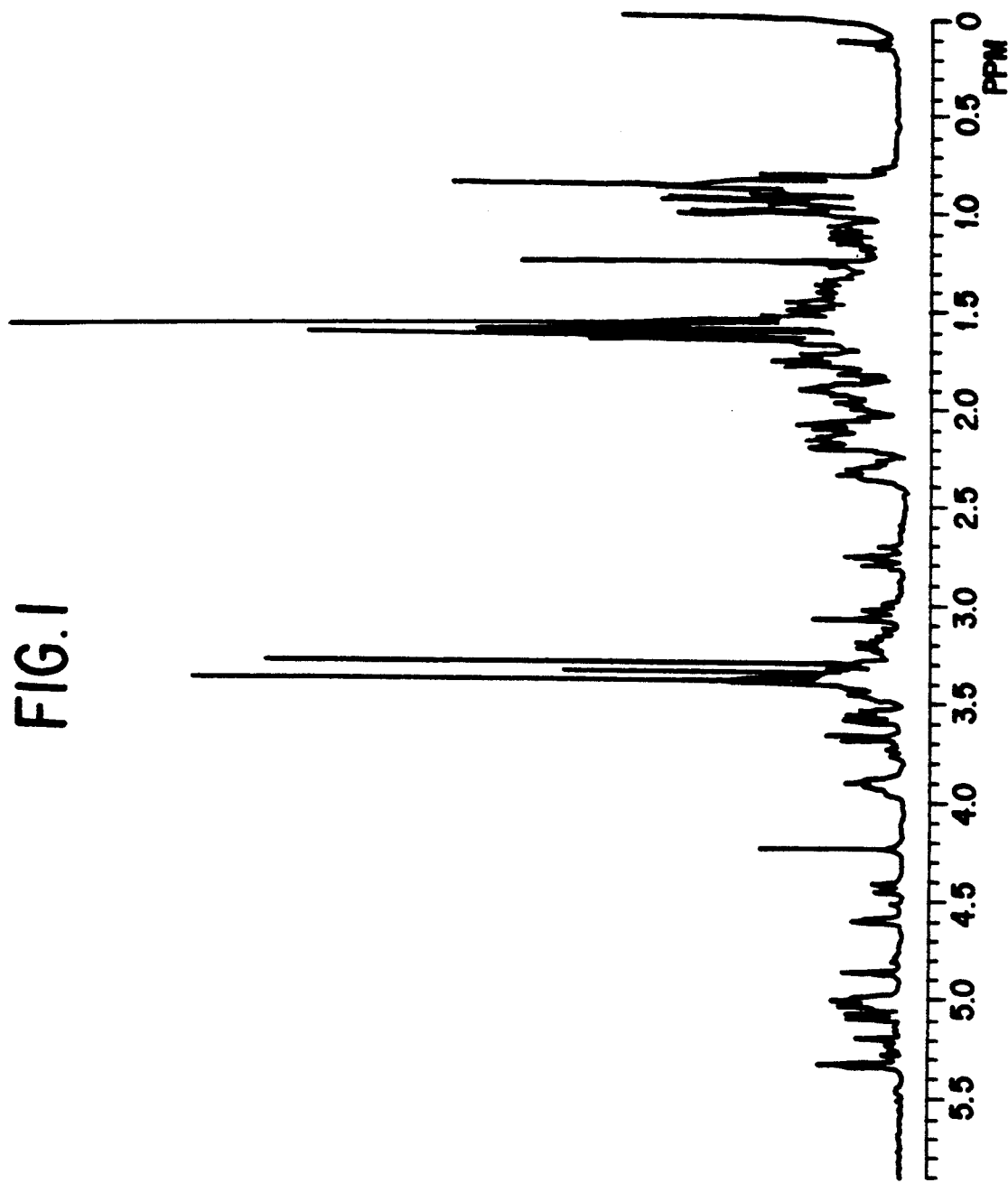
FIG. 1 is an $^1$H nuclear magnetic resonance (NMR) spectrum taken at 400 MHz of "demethimmunomycin" in CDCl$_3$.
Figure 1A:
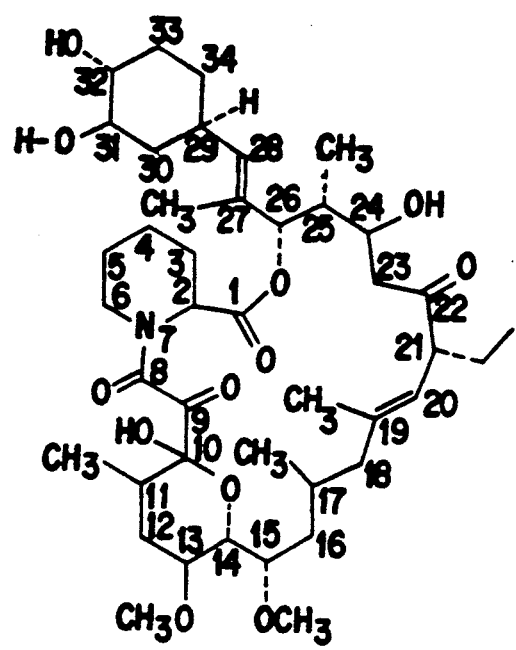
Figure 2:
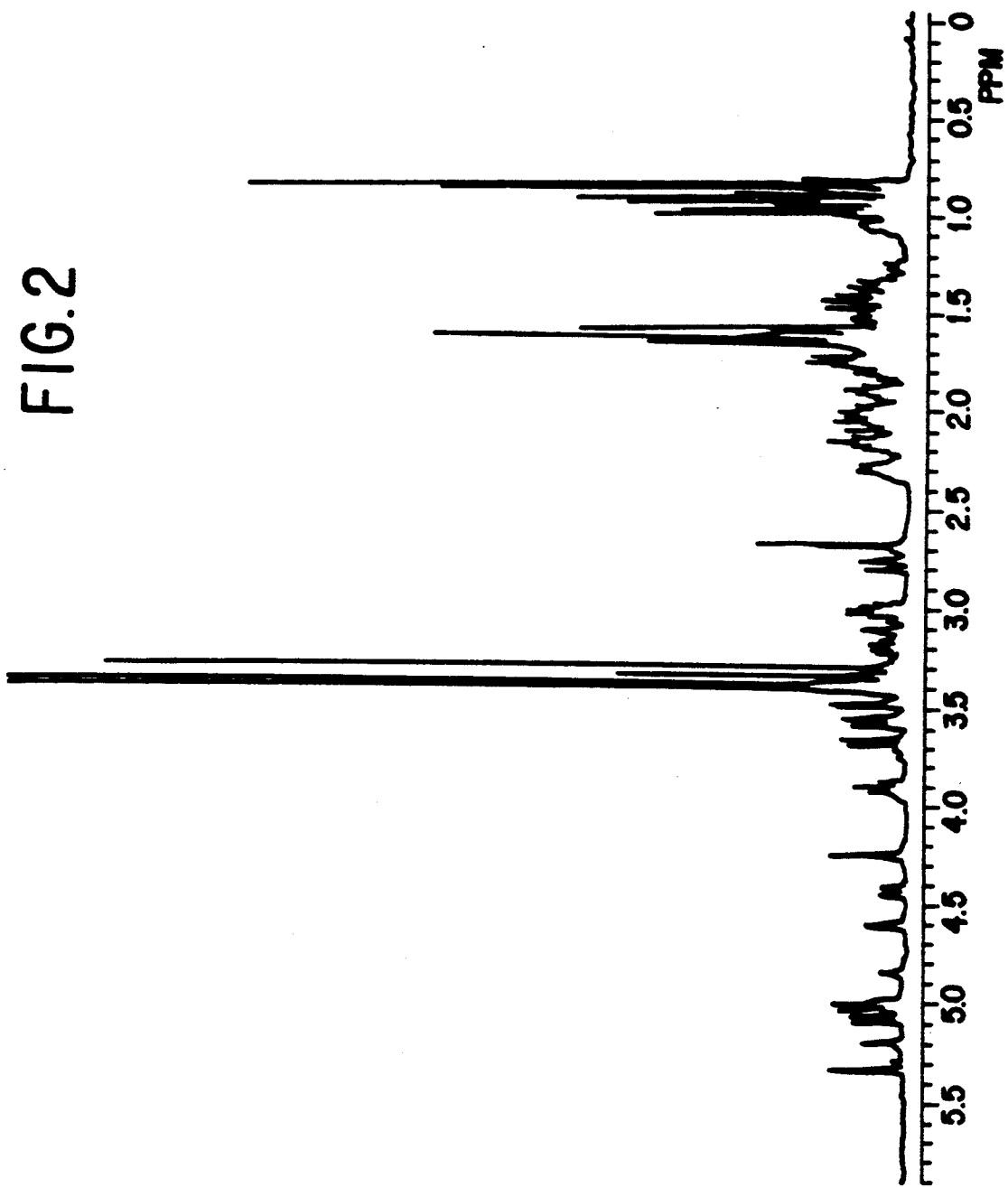
FIG. 2 is an $^1$H NMR spectrum taken at 400 MHz of L-683,590 in CDCl$_3$.
Figure 2A:
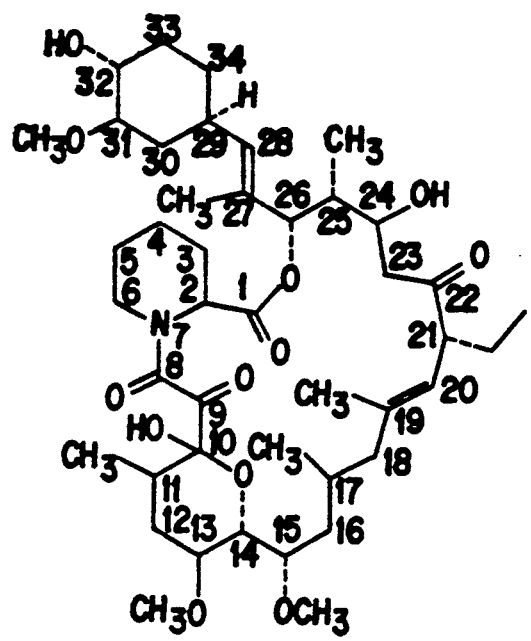
Figure 3:
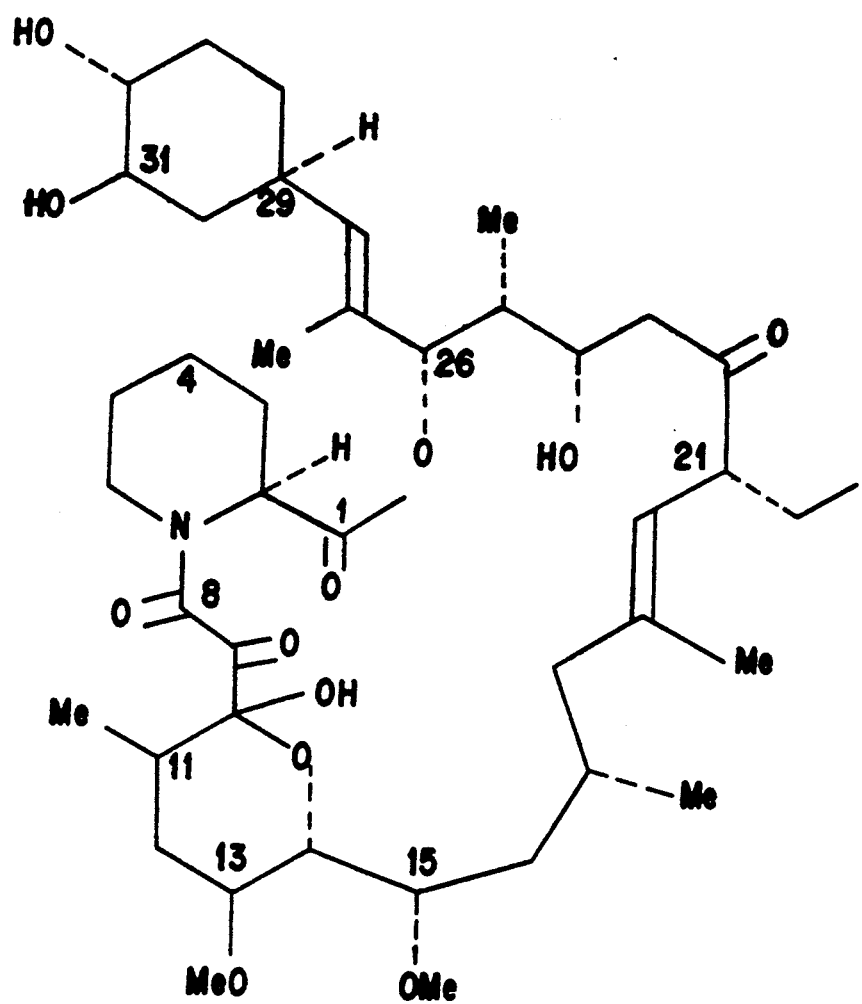
FIG. 3 is the assigned molecular structure of "demethimmunomycin".

The present invention involves the fermentation of *Streptomyces hygroscopicus* subsp. *ascomyceticus* ATCC No. 53855, to produce L-683,742. The microorganism is currently on restricted deposit filed Jan. 12, 1989, with the American Type Culture Collection, 12301 Parklawn Drive in Rockville, Md. as ATCC No. 53855, and in the Merck Culture Collection in Rahway, N.J. as MA 6646. The physical characteristics and taxonomy, including morphological, cultural, biological and physiological characteristics are briefly described hereinbelow.

STRAIN MA 6646

Microscopic observations—Branching filamentous mycelia 0.6 microns in diameter. Sporophores appear as short, compact spirals.

Oat Meal Agar

Vegetative Growth: Reverse: Greyish-white.
Aerial Mass: Abundant, matte, grey to black.
Soluble Pigment: None.

Glycerol-Asparagine

Vegetative Growth:
  Reverse: Off-white, translucent.
  Obverse: Off-white, translucent, erose edge.
Aerial Mycelium: Sparse, off-white, powdery.
Soluble Pigment: None.

Inorganic Salts-Starch Agar

Vegetative Growth: Reverse: cream-yellow.
Aerial Mass: Abundant, velvety, light grey to black.
Aerial Mycelium: White, velvety.
Soluble Pigment: None.

Yeast Extract-Malt Extract Agar

Vegetative Growth: Reverse: Greyish-yellow.
Aerial Mass: Abundant, light to medium grey, matte, cottony.
Soluble Pigment: None.

Carbohydrate Utilization Pattern

| d-glucose | ++ | d-maltose | + | sucrose | − |
|---|---|---|---|---|---|
| d-arabinose | +/− | d-mannitol | ++ | d-xylose | ++ |
| l-arabinose | +/− | d-mannose | ++ | l-xylose | − |
| d-fructose | ++ | l-mannose | − | alpha d-lactose | ++ |
| l-glucose | − | d-raffinose | − | beta d-lactose | ++ |
| inositol | +/− | l-rhamnose | ++ | | |

Where
++ indicates substantial growth;
+ indicates moderate growth;
+/− indicates trace growth; and
− indicates no growth.

The present invention process can be practiced with any "C-31 demethylating" strain of mutant *Streptomyces hygroscopicus* subsp. *ascomyceticus* and particularly preferred is the ATCC No. 53855 strain.

In general, L-683,742 can be produced by culturing (fermenting) the above-described mutant strain in an aqueous nutrient medium containing sources of assimilable carbon and nitrogen, preferably under submerged aerobic conditions (e.g. shaking culture, submerged culture, etc.). The aqueous medium is preferably maintained at a pH of about 7 at the initiation and termination (harvest) of the fermentation process. A higher pH leads to substantial and/or total loss of product. The desired pH may be maintained by the use of a buffer such as morpholinoethanesulfonic acid (MES), morpholinopropanesulfonic acid (MOPS), and the like, or by choice of nutrient materials which inherently possess buffering properties, such as production media described hereinbelow.

The preferred sources of carbon in the nutrient medium are carbohydrates such as glucose, xylose, galactose, glycerin, starch, dextrin, and the like. Other sources which may be included are maltose, rhamnose, raffinose, arabinose, mannose, salicin, sodium succinate, and the like.

The preferred sources of nitrogen are yeast extract, meat extract, peptone, gluten meal, cottonseed meal, soybean meal and other vegetable meals (partially or totally defatted), casein hydrolysates, soybean hydrolysates and yeast hydrolysates, corn steep liquor, dried yeast, wheat germ, feather meal, peanut powder, distiller's solubles, etc., as well as inorganic and organic nitrogen compounds such as ammonium salts (e.g. ammonium nitrate, ammonium sulfate, ammonium phosphate, etc.), urea, amino acids, and the like.

The carbon and nitrogen sources, though advantageously employed in combination, need not be used in their pure form, because less pure materials which contain traces of growth factors and considerable quantities of mineral nutrients, are also suitable for use. When desired, there may be added to the medium mineral salts such as sodium or calcium carbonate, sodium or potassium phosphate, sodium or potassium chloride, sodium or potassium iodide, magnesium salts, copper salts, cobalt salts, and the like. If necessary, especially when the culture medium foams seriously, a defoaming agent, such as liquid paraffin, fatty oil, plant oil, mineral oil or silicone may be added.

As to the conditions for the production of L-683,742 in massive amounts, submerged aerobic cultural conditions are preferred therefor. For the production in small amounts, a shaking or surface culture in a flask, bottle or culture dish is employed. Furthermore, when the growth is carried out in large tanks, it is preferable to use the vegetative form of the organism for inoculation in the production tanks in order to avoid growth lag in the process of production of L-683,742. Accordingly, it is desirable first to produce a vegetative inoculum of the organism by inoculating a relatively small quantity of culture medium with spores or mycelia of the organism produced in a "slant" and culturing said inoculated medium, also called the "seed medium", and then to transfer the cultured vegetative inoculum aseptically to large tanks. The fermentation medium, in which the inoculum is produced, is substantially the same as or different from the medium utilized for the production of L-683,742 and is generally autoclaved to sterilize the medium prior to inoculation. The pH of the medium is generally adjusted to about 7.0 prior to the autoclaving step by suitable addition of an acid or base, preferably in the form of a buffering solution.

Agitation and aeration of the culture mixture may be accomplished in a variety of ways. Agitation may be provided by a propeller or similar mechanical agitation equipment, by revolving or shaking the fermentor, by various pumping equipment or by the passage of sterile air through the medium. Aeration may be effected by passing sterile air through the fermentation mixture.

The fermentation is usually conducted at a temperature between about 20° C. and 40° C., preferably 25°-35° C., for a period of about 48 hours to 96 hours, which may be varied according to fermentation conditions and scales. Preferably, the production cultures are incubated for about 96 hours at 27° C. on a rotary shaker operating at 220 rpm, wherein the pH of the fermentation medium is maintained at 7.0 to harvest.

Preferred culturing/production media for carrying out the fermentation include the following:

|  | g/liter |
| --- | --- |
| Seed Medium A | |
| Glucose | 20.0 |
| Difco Yeast Extract | 20.0 |
| Hycase SF | 20.0 |
| KNO$_3$ | 2.0 |
| FeSO$_4$.7H$_2$O | 0.025 |
| NaCl | 0.5 |
| MgSO$_4$.7H$_2$O | 0.5 |
| MnSO$_4$.7H$_2$O | 0.005 |
| ZnSO$_4$.7H$_2$O | 0.01 |
| CaCl$_2$.2H$_2$O | 0.02 |
| Production Medium B | |
| Glucose | 22 |
| Glycerol | 25 |
| Corn Steep Liquor | 10 |
| Difco Yeast Extract | 15 |
| Lactic Acid | 2 |
| L-Tyrosine | 4 |
| MOPS | 10 |
| CaCO$_3$ | 0.25 |
| Adjust pH to 6.8 | |

The produced L-683,742, can be recovered from the culture medium by conventional means which are commonly used for the recovery of other known biologically active substances. The L-683,742 substance produced is found in the cultured mycelium and filtrate, and accordingly can be isolated and purified from the mycelium and the filtrate, which are obtained by filtering or centrifuging the cultured broth, by a conventional method such as concentration under reduced pressure, lyophilization, extraction with a conventional solvent, such as methanol and the like, pH adjustment, treatment with a conventional resin (e.g. anion or cation exchange resin, non-ionic adsorption resin, etc.), treatment with a conventional adsorbent (e.g. activated charcoal, silicic acid, silica gel, cellulose, alumina, etc.), crystallization, recrystallization, and the like. A preferred method is solvent extraction, particularly using methanol.

The product L-683,742 from the fermentation exhibits positive immunosuppressive activity by the "T-cell proliferation assay" and possesses utility on this basis.

The following examples are given for the purpose of illustrating the present invention and should not be construed as being limitations on the scope or spirit of the instant invention.

EXAMPLE 1

Mutagenesis and Culture Conditions

Spores of MA 6475 were prepared from Bennett's agar (Difco yeast extract, 0.1%, beef extract, 0.1%, N-Z Amine type A, 0.2%, glucose, 1%, and Agar, 1.5%) and were treated for 30 minutes with N-methyl-N'-nitro-N-nitrosoguanidine at a concentration of 2 mg/ml of TM-buffer (0.05M Tris, 0.05M maleic acid, adjusted to pH 9 with NaOH) at room temperature with gentle agitation. The treated spores were plated for single colonies on Bennett's agar. Methanol extracts of fermentations of these colonies were examined by thin layer chromatography (TLC) for mutant phenotypes. The subject mutant, MA 6646, was identified as an isolate which produced a major component which was more polar than the major parent compound (L-683,590) in the solvent system of chloroform:methanol (9:1). An HPLC profile showed that the peak corresponding to FK-523 in the parent culture was missing, that the peak corresponding to the major FK-520 peak in the parent culture was barely detectable, and that two new peaks with earlier retention times (than FK-520 and FK-523) had appeared.

Confirmation of the mutant phenotype was obtained by the fermentation, extraction and TLC and HPLC analyses of 12 reisolates of the original mutant "patch". The fermentation involved inoculating a 250 ml baffled Erlenmeyer flask containing 44 ml of an autoclaved seed medium prepared with distilled water and consisting of KNO$_3$, 0.2%, HyCase SF, 2%, Difco yeast extract, 2%, glucose, 2% FeSO$_4$•7H$_2$O, 0.0025%, NaCl, 0.05%, MgSO$_4$•7H$_2$O, 0.05%, MnSO$_4$•7H$_2$O, 0.0005%, ZnSO$_4$•7H$_2$O, 0.001%, and CaCl$_2$•2H$_2$O, 0.002%. The seed medium was inoculated with spores from Bennett's medium and incubated for 42-48 hours, at 27° C. on a rotary shaker operating at 220 rpm. A 1.0 ml aliquot of the resulting seed culture was used to inoculate a 250 ml non-baffled Erlenmeyer flask containing production medium prepared with distilled water and which consisted of glycerol, 2.5%, glucose, 2.2%, corn steep liquor, 1.5%, Difco yeast extract, 1.5%, lactic acid, 0.2% (v/v), L-tyrosine, 0.4%, MOPS, 1%, and CaCO$_3$, 0.025% where the pH was adjusted to pH 6.8 with NaOH prior to autoclaving. The production culture was incubated for 96 hours at 27° C. on a rotary shaker operating 220 rpm. A methanol extraction was achieved by addition of an equal volume of methanol to the broth culture, agitating at high speed on an Eberbach reciprocating shaker for 20 minutes followed by centrifugation. The aqueous methanolic extracts were analyzed by TLC and HPLC.

By reverse phase HPLC (Whatman Partisil 5 ODS-3, 0.1% aqueous H$_3$PO$_4$:CH$_3$CN, 40:60, 1 ml/min), the major component of all isolates had a retention time of 5.97 minutes relative to 7.97 minutes for FK-520. This component had the same retention time by HPLC and the same R$_f$ by TLC as 31-desmethyl-L-683,590 (L-683,742).

For structure determination, the compound was isolated on a semi-preparative reverse phase octadecyl C$_{18}$ HPLC column (Whatman Magnum 9, Partisil 10 ODS-3). Four shake flask cultures of the mutant were extracted with an equal volume of methanol, centrifuged, and the supernatant evaporated to remove the methanol. The resulting aqueous phase was extracted twice with methylene dichloride and evaporated to dryness under a stream of nitrogen. The residue was resuspended in methanol and a 1 ml aliquot was injected onto the semi-preparative column. The solvent system was H$_2$O:CH$_3$CN (40:60) at a flow rate of 3 ml/min. The broad peak eluting between 9.4 and 12 minutes was collected, evaporated under a stream of nitrogen and resuspended in 1 ml of methanol. The concentration of the sample was estimated by analytical HPLC to be approximately 4.5 mg/ml. A dilution of this sample was submitted for IL-2 assay. The results showed that the diluted sample exhibited positive immunosuppressive activity. NMR analysis determined that the compound produced by the mutant strain was the same as L-683,742.

It is reasonably believed that a mutation in the C-31 O-methyltransferase gene has inactivated the immunomycin C-31 O-methyltransferase resulting in the efficient production of L-683,742. It is further noted that this mutation has not affected the O-methylation at C-13 and C-15 indicating that a different protein, or proteins, is responsible for the O-methylation at these positions in L-683,742 and L-683,590.

What is claimed is:

1. A process for directly producing an immunosuppressant L-683,742, comprising culturing *Streptomyces hygroscopicus* subsp. *ascomyceticus* ATCC No. 53855 under submerged aerobic fermentation conditions in an aqueous nutrient medium containing assimilable sources of carbon, nitrogen and inorganic substances at a pH below 8.0 for a sufficient time to produce L-683,742, and recovering the L-683,742 from the medium.

* * * * *